(12) United States Patent
Clouatre et al.

(10) Patent No.: US 7,015,250 B2
(45) Date of Patent: Mar. 21, 2006

(54) METHODS AND PHARMACEUTICAL PREPARATIONS FOR NORMALIZING BLOOD PRESSURE WITH (-)-HYDROXYCITRIC ACID

(75) Inventors: Dallas L. Clouatre, Menlo Park, CA (US); James M. Dunn, Littleton, CO (US)

(73) Assignee: Glykon Technologies Group, LLC, Las Vegas, NV (US)

( * ) Notice: Subject to any disclaimer, the term of this patent is extended or adjusted under 35 U.S.C. 154(b) by 0 days.

(21) Appl. No.: 09/781,491

(22) Filed: Feb. 13, 2001

(65) Prior Publication Data

US 2001/0044469 A1     Nov. 22, 2001

Related U.S. Application Data

(60) Provisional application No. 60/181,285, filed on Feb. 9, 2000.

(51) Int. Cl.
    *A61K 31/19*     (2006.01)
(52) U.S. Cl. ..................................... 514/574; 514/557
(58) Field of Classification Search ................ 514/574
See application file for complete search history.

(56) References Cited

U.S. PATENT DOCUMENTS

| | | | | |
|---|---|---|---|---|
| 3,764,692 | A | 10/1973 | Lowenstein ................. | 424/279 |
| 3,767,678 | A | 10/1973 | Guthrie et al. ............ | 260/343.6 |
| 3,919,254 | A | 11/1975 | Guthrie et al. ............ | 260/343.6 |
| 3,993,668 | A | 11/1976 | Guthrie et al. ............ | 260/343.6 |
| 5,626,849 | A * | 5/1997 | Hastings et al. ............ | 514/188 |
| 5,656,314 | A | 8/1997 | Moffett et al. .............. | 426/279 |
| 5,783,603 | A | 7/1998 | Majeed et al. .............. | 514/574 |
| 5,914,326 | A | 6/1999 | McCarty et al. ............ | 514/188 |
| 6,221,901 | B1 * | 4/2001 | Shrivastava et al. ........ | 514/458 |

FOREIGN PATENT DOCUMENTS

EP           803202 A2 * 10/1997
IT           0803202 A2 * 10/1997

OTHER PUBLICATIONS

DiPiro et al., Editor, Pharmacotherapy, A Pathophysiologic Approach, 1989, pp. 805-811.*
Solomons, T. W. G., Organic Chemistry, 3rd Edition, 1984, pp. 799-800.*
McMurry, J., Organic Chemistry, 2nd Edition, 1988, pp. 759-767.*
Sullivan, A. C. et al., "Metabolic Regulation as a Control for Lipid Disorders. I. Influence of (-)-Hydroxycitrate on Experimentally Induced Obesity in the Rodent" The American Journal of Clinical Nutrition,30: May 1977, pp. 767-776.*
Hardman, J.G. editor-in-chief, of Goodman and Gilman's The Pharmacological Basis of Therapeutics, 9th Edition, p. 803-804, 1996.*
DiPiro et al. Editor, Pharmacotherapy, A Pathophysiologic Approach, 1989, pp. 97-102 and 805-811, 1989.*
Solomons, T. W. G., Organic Chemistry, 3rd Edition, 1984, pp. 799-800.*
McMurry, J. Organic Chemistry, 2ND Edition, 1988, pp. 759-767.*
Benson S, Vance-Bryan K, Raddatz J. Time to patient discontinuation of antihypertensive drugs in different classes. Am J Health Syst Pharm. Jan. 1, 2000 ;57(1):51-4.
Cusin I, Rohner-Jeanrenaud F, Terrettaz J, Jeanrenaud B. Hyperinsulinemia and its impact on obesity and insulin resistance. Int J Obes Relat Metab Disord. Dec. 1992;16 Suppl 4:S1-11.
Ishihara K, Oyaizu S, Onuki K, Lim K, Fushiki T. Chronic (-)-hydroxycitrate administration spares carbohydrate utilization and promotes lipid oxidation during exercise in mice. J Nutr. Dec. 2000;130(12):2990-5.
McCarty MF. Toward a wholly nutriontional therapy for type 2 diabetes. Med Hypotheses Mar. 2000;54(3):483-487.
McCarty MF. Promotion of hepatic lipid oxidation and gluconeogenesesis as a strategy for appetite control. Medical Hypotheses 1994;42:215-225.
Preuss HG, Burris JF. Adverse metabolic effects of antihypertensive drugs. Implications for treatment. Drug Saf. Jun. 1996;14(6):355-64.
Sowers JR, Bakris GL. Antihypertensive therapy and the risk of type 2 diabetes mellitus. N Engl J Med. Mar. 30, 2000;342(13):969-70.
Sullivan AC, Triscari J. Metabolic regulation as a control for lipid disorders. I. Influence of (-)-hydroxycitrrate on experimentally induced obesity in the rodent. American Journal of Clinical Nutrition 1977;30:767.
Sullivan, Ann C. and Joseph Triscari. Possible interrelationship between metabolite flux and appetite. In D. Novin, W. Wyriwicka and G. Bray, eds., Hunger: Basic Mechanisms and Clinical Implications (New York: Raven Press,1976) 115-125.

* cited by examiner

*Primary Examiner*—Dwayne Jones
(74) *Attorney, Agent, or Firm*—Michel Morency; James F. Ewing; Foley & Lardner LLP

(57) ABSTRACT

A method whereby the blood pressure metabolism in an individual showing evidence of dysregulation is improved when that person receives an appropriate oral administration of (–)-hydroxycitric acid. The potassium salt of (–)-hydroxycitric acid is a preferred form of the compound, followed by the sodium salt, then by the amide and other derivatives of the acid. The regulation of blood pressure levels over any given period of time may be improved with a controlled release form of (–)-hydroxycitric acid. Controlled release can be used to provide a sustained and modulated amount of the active to the body as desired and therefore regulate the use of the compound as a hypotensive agent.

18 Claims, No Drawings

METHODS AND PHARMACEUTICAL PREPARATIONS FOR NORMALIZING BLOOD PRESSURE WITH (-)-HYDROXYCITRIC ACID

PROVISIONAL PATENT APPLICATION FILING

This application is entitled to the benefit of Provisional Patent Application Ser. No. 60/181,285 filed Feb. 9, 2000 "Methods And Pharmaceutical Preparations For Normalizing Blood Pressure With (−)-Hydroxycitric Acid"

BACKGROUND OF THE INVENTION

1. Field of the Invention

The invention is directed toward the use of (−)-hydroxycitric acid, especially as potassium (−)-hydroxycitrate, a preferred salt of (−)-hydroxycitric acid, to reduce ("normalize") elevated blood pressure in individuals in need thereof.

2. Description of Prior Art

Hypertension is defined as an average or sustained systolic blood pressure over 140 mm Hg and/or a diastolic blood pressure over 90 mm Hg. Hypertension has an overall incidence of 20%, with onset usually occurring after age 20. The prevalence rises with age to over 50% past age 65. Ninety-five to 99% of hypertensive individuals have essential hypertension. Persons with hypertension are three to four times more likely to experience a major cardiovascular event (e.g., myocardial infarction, cerebrovascular accident, congestive heart failure) than those without.

Essential, or primary, hypertension is often said to have no identifiable cause. However, this belies the fact that risk factors long have been identified. Hypertension is more common in African Americans at all ages and in persons from lower socioeconomic groups. Individual risk factors include family history, excessive alcohol consumption, high sodium intake, stress, sedentary lifestyle, obesity and a high intake of sugars (sucrose, fructose, glucose, etc.) Hypertension is one of the disorders which are linked to insulin resistance and elevated insulin levels. Hypertension is also linked to the excessive production of "stress hormones," such as cortisol and corticosterone. Long-term stress is known to elevate aldosterone levels and thereby to increase sodium retention, a source of hypertension.

The various drug therapies available to treat hypertension have many drawbacks and preponderantly are unsatisfactory in cases of mild to moderate symptoms. Drug therapy is recommended for patients with sustained systolic pressure over 160 mm Hg or diastolic pressure over 100 mm Hg. Traditionally, therapy with a diuretic or beta-blocker is tried first. The dosage may be modified or an additional drug from another class may be added. Ten percent of patients may require three drugs. Diuretics—e.g., hydrochlorothiazide (Hydrodiuril; 12.5 to 50 mg/day)—have side effects which include a decreased level of potassium and increased cholesterol and glucose levels; contraindicated in patients with gout and diabetes. Potassium-sparing agents—e.g., spironolactone (Aldactazide; 25 to 100 mg/day)—have side effects which include hyperkalemia and gynecomastia.

Numerous other classes of hypotensive drugs presently are in use. Most cause a variety of undesirable effects. Alpha-blockers—e.g., doxazosin (Cardura; 1 to 20 mg/day)—have side effects which include postural hypotension and lassitude. Beta-blockers—e.g., acebutolol (Sectral; 200 to 800 mg/day)—have side effects which include congestive heart failure, bronchospasm, the masking of hypoglycemia induced by insulin, depression, insomnia and fatigue; these are contraindicated relatively in heart failure, airway disease, heart block, diabetes, and peripheral vascular disease. Alpha/beta blockers—e.g., labetalol (Normodyne; 200 to 1,200 mg/day in two doses)—have side effects which include postural hypotension and beta-blocker side effects. Centrally acting sympatholytics—e.g., methyldopa (Aldomet; 500 to 3,000 mg/day in two doses)—have side effects which include hepatic disorders, sedation and dry mouth. Peripherally acting sympatholytics—e.g., reserpine (Serpasil; 0.05 to 0.25 mg/day)—have side effects which include sedation and depression. Calcium-channel blockers—e.g., verapamil (Isoptin; 90 to 480 mg/day)—have side effects which include constipation, nausea, headache and conduction defects; these must be used with caution in heart failure or blockage. Dihydropyridines—e.g., amlodipine (Norvase; 2.5 to 10 mg/day)—have side effects which include flushing, headache and ankle edema. Direct vasodilators—e.g., hydralazine (Apresoline; 50 to 400 mg/day in two doses)—have side effects which include headache, tachycardia and lupus syndrome. Angiotensin-converting enzyme (ACE) inhibitors—e.g., benazepril (Lotensin; 5 to 40 mg/day)—have side effects which include cough, rash and loss of taste; these should be used with caution in renovascular disease.

Roughly one half of all patients who are treated for hypertension stop complying with their drug treatment regimens within the first year of therapy, with many stopping within the first three months. Only an estimated 50–74% of the U.S. populace with hypertension is presently receiving treatment and, within this category of treated patients, only 50% find that their hypertension is adequately controlled by drugs. Of the drugs popularly employed, compliance rates over the long term appear to be greatest with the angiotensin-converting enzyme (ACE) inhibitors, followed in succession by the calcium-channel blockers, β-blockers and the diuretics. (Benson S, Vance-Bryan K, Raddatz J. Time to patient discontinuation of antihypertensive drugs in different classes. Am J Health Syst Pharm. Jan. 1, 2000; 57(1):51–4.) Unfortunately, β-blockers definitely increase the risk of developing diabetes Type 2, and diuretics may similarly a increase this risk. Both classes of drugs may increase insulin resistance, LDL-cholesterol and triglycerides. (Sowers J R., Bakris G. L. Antihypertensive therapy and the risk of type 2 diabetes mellitus. N Engl J Med. Mar. 30, 2000; 342(13): 969–70.) (Preuss H G., Burris J F. Adverse metabolic effects of antihypertensive drugs. Implications for treatment. Drug Saf. Jun. 14, 1996; (6):355–64.)

(−)-Hydroxycitric acid (abbreviated herein as HCA) a naturally-ocurring substance found chiefly in fruits of the species of *Garcinia,* and several synthetic derivatives of citric acid have been investigated extensively in regard to their ability to inhibit the production of fatty acids from carbohydrates, to suppress appetite, and to inhibit weight gain. (Sullivan A C, Triscari J. Metabolic regulation as a control for lipid disorders. I. Influence of (−)-hydroxycitrrate on experimentally induced obesity in the rodent. American Journal of Clinical Nutrition 1977; 30:767.) Weight loss benefits were first ascribed to HCA, its salts and its lactone in U.S. Pat. No. 3,764,692 granted to John M. Lowenstein in 1973. The claimed mechanisms of action for HCA, most of which were originally put forth by researchers at the pharmaceutical firm of Hoffmann-La Roche, have been summarized in at least two United States Patents. In U.S. Pat. No. 5,626,849 these mechanisms are given as follows: "(−) HCA reduces the conversion of carbohydrate calories into fats. It does this by inhibiting the actions of ATP-citrate lyase, the enzyme which converts citrate into fatty acids and cholesterol in the primary pathway of fat synthesis in the body. The actions of (−) HCA increase the production and storage of glycogen (which is found in the liver, small intestine and muscles of mammals) while reducing both appetite and weight gain. (−) Hydroxycitric acid also causes calories to be burned in an energy cycle similar to thermogenesis . . . (−) HCA also increases the clearance of LDL cholesterol . . . " U.S. Pat. No. 5,783,603 further argues that HCA serves to disinhibit the metabolic breakdown and oxidation of stored fat for fuel via its effects upon the compound malonyl CoA and that gluconeogenesis takes place as a result of this action. The position that HCA acts to unleash fatty acid oxidation by negating the effects of malonyl CoA with gluconeogenesis as a consequence (McCarty M. F. Promotion of hepatic lipid oxidation and gluconeogenesis as a strategy for appetite control. Medical Hypotheses 1994; 42:215–225) is maintained in U.S. Pat. No. 5,914,326. The gluconeogenesis expected by these authors would normally lead to an increase in insulin resistance, an increase in insulin levels and, as a consequence, an increase in the rate of hypertension which is strongly linked to insulin resistance and elevated insulin levels. Hyperinsulinemia is itself a pathological driving force in producing incipient obesity and incipient muscle insulin resistance. (Cusin I, Rohner-Jeanrenaud F, Terrettaz J, Jeanrenaud B. Hyperinsulinemia and its impact on obesity and insulin resistance. Int J Obes Relat Metab Disord. Dec. 16, 1992; Suppl 4:S1–11.) In general, the higher the fasting plasma insulin levels, the more likely the presence of hypertension. (Preuss H G., Burris J F. Adverse metabolic effects of antihypertensive drugs. Implications for treatment. Drug Saf. Jun. 14, 1996; (6):355–64.)

Unknown in the scientific literature is the unusual and surprising ability of HCA to reduce elevated blood pressure. This is a normalizing effect, and there is no evidence nor is there any reason to suspect that the ingestion of HCA will induce low blood pressure in individuals whose blood pressure is already within the normal range. The benefits of HCA in reducing hypertension are especially pronounced in the preferred salt of the acid, potassium hydroxycitrate, and may be further potentiated by the use of a controlled-release form of the compound. Moreover, the authors have found that HCA is a safe hypotensive. Its benefits appear gradually over the course of several weeks and do not seem to be the result of any direct manipulation of nitric oxide production nor of renal function (i.e., diuresis per se is not involved).

The proposed mechanisms by which HCA achieves its hypotensive effect are a reduction in blood insulin levels, a reduction in corticosterone (stress hormone) levels and a long term reduction in the levels of the mineralocorticoids, as well. It is well established that chronic stress leads to chronically elevated levels of glucocorticoids (predominantly cortisol in humans and corticosterone in rodents) and that elevations of aldosterone ultimately follow. The glucocorticoids contribute to insulin resistance by simultaneously promoting both gluconeogenesis (glucose production from noncarbohydrate sources) and lipolysis (the release of free fatty acids) while slowing the oxidation of glucose and sacrificing lean tissue as a source of gluconeogenic precursors, i.e., the chronic elevation of glucocorticoids ultimately is catabolic in its impact upon lean tissues. Elevated blood glucose concentrations are an accepted result of these actions. The compensatory release of mineralocorticoids, such as aldosterone, in response to the chronic elevation of glucocorticoid levels increases sodium retention, and hence blood pressure. All of these factors are known causes of elevated blood pressure.

Quite surprisingly, this effect of HCA has never been mentioned in the literature on the topic. Indeed, those authorities who hold that HCA is gluconeogenic in its actions and primarily useful for increasing ketogenesis typically view it as potentially raising blood sugar levels rather than reducing them and thereby also likely to increase insulin levels. The implied consequence is an increased risk of hypertension. The original pharmaceutical research on HCA performed at Hoffman-La Roche failed to find significant changes in either blood glucose levels or blood insulin levels, undoubtedly in large part due to the fact that almost all of that research used diets which consisted mostly of glucose (e.g., 70% glucose diets were typically employed to encourage lipogenesis). The conclusion of the Roche researchers was that "no significant differences in plasma levels of glucose, insulin, or free fatty acids were detected in (−)-hydroxycitrate-treated rats relative to controls. These data suggest that peripheral metabolism, defined in the present context as metabolite flux, may be involved in appetite regulation . . . " (Sullivan, Ann C. and Joseph Triscari. Possible interrelationhip between metabolite flux and appetite. In D. Novin, W. Wyriwicka and G. Bray, eds., Hunger: Basic Mechanisms and Clinical Implications (New York: Raven Press,1976) 115–125.)

There is evidence from animal studies, but not from any good human study, that ingested HCA will lower cholesterol blood lipids levels, but much less attention has been paid to free fatty acids. It is known that high levels of circulating free fatty acids are often related to insulin resistance and thereby to elevated blood pressure. Paradoxically for some theories of hypertension, HCA may exercise no effect on or actually increase free fatty acid levels (Ishihara K, Oyaizu S, Onuki K, Lim K, Fushiki T. Chronic (−)-hydroxycitrate administration spares carbohydrate utilization and promotes lipid oxidation during exercise in mice. J Nutr. December 2000; 130(12):2990–5) despite the fact, as the inventors have discovered, that it lowers insulin levels and blood pressure. And, indeed, the issue of blood pressure appears to not be a part of discussions of the effects of HCA. (McCarty M. F. Toward a wholly nutritional therapy for type 2 diabetes. Med Hypotheses March 2000; 54(3):483–487; U.S. Pat. No. 6,113,949; U.S. Pat. No. 5,914,326; U.S. Pat. No. 5,783,603; U.S. Pat. No. 5,626,849.)

Only the potassium and sodium salts of HCA are absorbed well enough to be effective agents at tolerable levels of ingestion. Reasons for this are given in the inventors' copending U.S. Patent Application "Potassium (−)-Hydroxycitric Acid Methods For Pharmaceutical Preparations For Stable And Controlled Delivery." Derivatives of HCA may also be active and effective in this regard. (U.S. Pat. Nos. 3,993,668; 3,919,254; 3,767,678.) The calcium salt of HCA is extremely widely sold in the United States in dosages ranging up to more than 12 grams per day (providing roughly 6 grams of HCA), and yet there are no reports in the literature of this salt being useful as a hypotensive agent. Liquid forms of HCA currently in use are irritating to the digestive system, depending upon the dose, and may cause distress when used to achieve hypotensive or other purposes. Researchers have found that animals fed high doses of the liquid form of the compound exhibit stress behavior. (Ishihara K, Oyaizu S, Onuki K, Lim K, Fushiki T. Chronic (−)-hydroxycitrate administration spares carbohydrate utilization and promotes lipid oxidation during exercise in mice. J Nutr. December, 2000; 130(12):2990–5.) Similarly, the ethylenediamine salts of HCA used in much of the research performed by Hoffman-La Roche are known to be irritating and even toxic, properties which are due to the ethylenediamine ligand and not to the HCA.

In contrast to the quite limited efficacy found with the calcium salt and some other delivery forms of HCA, the impact of ingestion of appropriate amounts of the appropriate salts of HCA upon subjects with elevated blood pressure has been positive, as has the impact upon insulin levels and corticosterone levels in diets which calorically are not almost exclusively composed of sugars. No prior art suggests this beneficial effect of HCA upon blood pressure, insulin levels or stress hormone levels.

SUMMARY OF THE INVENTION

The inventors have discovered that HCA is useful in normalizing elevated blood pressure. This action by HCA has not heretofore been recognized. The benefits of HCA in reducing hypertension are especially pronounced in the preferred salt of the acid, potassium hydroxycitrate, and may be further potentiated by the use of a controlled-release form of the compound. The discovery that HCA has blood pressure moderating effects allows the creation of novel and more efficacious approaches to controlling mild hypertension, a condition which is otherwise not suitably treated through drug intervention. It may further offer an avenue by which individuals suffering from more severe hypertension may reduce the degree of drug intervention required (with its numerous side effects) or even be weaned from other medications entirely. The discovery that HCA can reduce the inappropriate release of stress hormones and reduce excessive insulin levels makes this compound especially useful for those populations which suffer from salt-sensitive hypertension and those individuals who suffer from insulin resistance due to chronic hyperinsulinemia. HCA is effective at a daily dosage (divided) of between 750 mg and 10 grams, preferably at a dosage of between 3 and 6 grams.

Objects and Advantages

It is an objective of the present invention to provide a method of for treating or ameliorating hypertension by providing a means of reducing elevated blood pressure levels. It is a further object of the present invention to provide a means of stabilizing blood pressure by ameliorating two of the primary causes of hypertension, that is, elevated insulin levels and elevated stress hormone levels. It is yet a further advantage of the present invention to provide a means—one which is accompanied by few or no side effects—of reducing elevated blood pressure. Knowledge of the present invention has the advantage of allowing the use of forms of (−)-hydroxycitric acid as hypotensive drugs, including especially through controlled release formulations. A further advantage of the present invention is to allow the employment of effective amounts and forms of HCA for reducing elevated blood pressure such that one extremely common drawback of presently available hypotensive drugs—early and widespread discontinuation of usage by patients—can be overcome.

DESCRIPTION OF THE PREFERRED EMBODIMENTS

The free acid form and various salts of (−)-hydroxycitric acid (calcium, magnesium, potassium and sodium) have been available commercially for several years. Any of these materials can be used to fulfill the invention revealed here, but with varying degrees of success. For reasons given in our copending U.S. Patent Application "Potassium (−)-Hydroxycitric Acid Methods For Pharmaceutical Preparations For Stable And Controlled Delivery," these materials are generally useful in this descending order of efficacy: potassium salt, sodium salt, free acid, magnesium salt, calcium salt. A novel method for improving the efficacy and workability of these forms is provided in that application. Exact dosing will depend upon the form of HCA used, the weight of the individual involved, and the other components of the diet. In part due to the need to control the release of this hypoglycemic agent in diabetics, as outlined in the inventors' recently issued United States Patent covering the employment of HCA as hypoglycemic agent, a controlled release preparation is to be preferred. Controlled release can also be expected to improve results by aiding in maintaining a sustained exposure to the drug as required for therapy.

The previously patented hydroxycitric acid derivatives (mostly amides and esters of hydroxycititric acid, the patents for which are now expired, to wit, U.S. Pat. Nos. 3,993,668; 3,919,254; and 3,767,678) likely are roughly equivalent to the HCA sodium salt in efficacy and can be applied as hypotensive agents as taught herein by one skilled in the art. However, for the purposes of reducing stress hormone levels and blood pressure, hydroxycitric acid in its free acid form and in its lactone form may prove to be the least desirable of currently available forms of the compound. These forms are irritating to the gastrointestinal tract and thus, in higher dosages, may lead to elevations in stress response. Similarly, hydroxycitric acid in its free acid form and in its lactone form are less desirable for long term use due to their ability to chelate minerals and thereby perhaps lead to mineral loss.

EXAMPLE 1

Blood pressure data was acquired from a multi-week pilot open clinical weight loss trial with extremely obese patients which was undertaken to gauge the effects of a pouch delivery form of a potassium salt of (−)-hydroxycitrate under the normal circumstances faced in clinical practice with this patient population. Sixteen patients were enrolled, three of whom were diabetics on medications or insulin. Several others were suspected of suffering from insulin resistance. The patients ingested 3–4 grams of HCA per day in two divided doses. Aside from being informed that they must eat a carbohydrate-containing meal within one hour of taking the HCA and that they should avoid eating late in the day, they were not instructed to follow any special diet or exercise plan outside their normal habits and no caloric restriction was imposed. This particular form of potassium (−)-hydroxycitrate delivery typically was mixed into water or juice and consumed at mid-morning and mid-afternoon. The delivery was a water-soluble immediate release form. It was a pre-commercial preparation and nearly all of the patients complained regarding the inconvenience and poor taste of the product, albeit there were no other issues of tolerability. A number of patients continued on the program for 6 weeks. However, most patient data was good for only 3 weeks because two of the diagnosed diabetics experienced severe hypoglycemic reactions. Several other patients experienced good appetite suppression, yet also complained of episodic tiredness at the beginning of the program, a sign of low blood sugar. Two patients subsequently were placed on phentermine. One patient who followed the program for 10 weeks with excellent weight loss (32 pounds over 10 weeks) found that his tendency toward elevated blood sugar was stabilized during the program. This patient returned to his prior experiences of infrequent hypoglycemia roughly one week after he had left the program, something which suggests a carryover effect from the compound. The average weight loss over the 3 week period for these 14 patients was approximately 3.1 pounds per person per week. The clinical decision was made that potassium (−)-hydroxycitrate in an immediate release format can exercise a strong hypoglycemic effect in diabetics and that it appears to influence blood sugar levels in protodiabetics, as well. At therapeutically effective dosages, HCA probably should be used with diabetic populations only under a physician's care.

Along with the hypoglycemic effect of the potassium hydroxycitrate, a quite surprising finding was that blood pressure levels in eight patients began to normalize rapidly with this treatment. Elevated blood pressure is common with obese and insulin-resistant patients, and therefore it was unremarkable that in this patient population (ages ranging roughly 30 to 60) that almost one half suffered from hypertension. Following are the readings for the eight hypertensive patients. Many of these patients had been advised to lower salt intake and to increase potassium and magnesium intake. Nevertheless, these results are so striking as to be unlikely limited to minor dietary modifications and a short-term increased intake of potassium and magnesium.

|  | Starting Blood Pressure | Ending Blood Pressure |  |
| --- | --- | --- | --- |
| Patient #1 | 150/88 | 138/70 | (wk 2) |
| Patient #2 | 178/100 | 130/80 | (wk 3) |
| Patient #3 | 130/98 | 120/72 | (wk 9) |
| Patient #4 | 150/98 | 110/80 | (wk 5) |
| Patient #5 | 140/78 | 126/80 | (wk 3) |
| Patient #6 | 180/88 | 160/70 | (wk 3) |
| Patient #7 | 120/80 | 120/70 | (wk 6) |
| Patient #8 | 170/100 | 160/100 | (wk 3) |

EXAMPLE 2

The results in Example 1 were unexpected from the published literature on HCA. Our clinical experience was that as little as 3 grams of HCA per day in divided doses in the form of potassium (−)-hydroxycitrate (5 grams of the salt) may exert a significant hypotensive effect which manifests over a period of one to several weeks. The available literature supplies no mechanisms by which to explain this effect.

Therefore, animal tests were scrutinized to determine if variations in serum levels of non-esterified fatty acids (NEFA), insulin and corticosterone could explain the novel findings. Ten-week old male rats were placed on a moderate fat diet (30% of calories, which is a high-fat diet for rats) for 60 days. These rats were fed water or potassium hydroxycitrate (0.33 mmols/kg) twice daily by gastric intubation, but were otherwise provided with food and water ad libitum. Five animals were used as controls and two different formulas of potassium hydroxycitrate were provided to five animals each. At the termination of the trial, data was collected as summarized in the following table. The differences between control (5 data points) and active (10 data points) were then analyzed according to the student's T test. There was no significant difference between control and the HCA groups with regard to NEFA. However, insulin levels in the animals given HCA were significantly lower than in controls, with a one-tailed P value of 0.0306; in the two-tailed test, P was just short of significance at 0.0612 because of the small number of animals. Corticosterone levels (essentially equivalent to cortisol—the "stress" hormone—levels in humans) were very significantly lower in the HCA groups than in control, with a one-tailed P value of 0.0013 and a two-tailed P value of 0.0026. Both of these factors could play a role in the clinical findings of lowered blood pressure in hypertensive individuals. Elevated insulin levels are known to be associated with hypertension. Glucocorticoids, similarly, are associated with hypertension through a variety of mechanisms, including sodium retention.

| Group | NEFA mmol/L | Insulin ng/mL | Corticosterone ng/mL |
| --- | --- | --- | --- |
| Control | 0.49 | 2.655 | 269.38 |
| Control | 0.33 | 7.077 | 497.87 |
| Control | 0.31 | 4.280 | 265.71 |
| Control | 0.29 | 9.425 | 209.54 |
| Control | 0.30 | 3.798 | 116.12 |
| KHCA 1 | 0.31 | 3.880 | 45.79 |
| KHCA 1 | 0.48 | 4.399 | 33.10 |
| KHCA 1 | 0.32 | 3.181 | 65.57 |
| KHCA 1 | 0.27 | 3.210 | 55.40 |
| KHCA 1 | 0.33 | 3.639 | 84.62 |
| KHCA 2 | 0.41 | 4.427 | 26.02 |
| KHCA 2 | 0.41 | 4.301 | 270.83 |
| KHCA 2 | 0.59 | 3.245 | 45.44 |
| KHCA 2 | 0.37 | 3.695 | 45.63 |
| KHCA 2 | 0.46 | 2.053 | 38.04 |

CONCLUSIONS (−)-Hydroxycitrate has a multitude of metabolic functions. The literature teaches that the compound reduces blood lipids, induces weight loss and decreases appetite in both animals and humans. However, the inventors have discovered that this compound is also a hypotensive agent which reduces insulin levels and stress hormone levels. This is an entirely novel use of (−)-hydroxycitric acid, its derivatives and its salt forms.

We claim:

1. A method for treating or ameliorating hypertension or high blood pressure in individuals in need thereof which is comprised of administering orally an effective amount of (−)-hydroxycitric acid.

2. A method for treating or ameliorating hypertension or high blood pressure by lowering elevated insulin in individuals in need thereof which is comprised of administering orally an effective amount of (−)-hydroxycitric acid.

3. A method for treating or ameliorating hypertension or high blood pressure by lowering elevated glucocorticoid levels in individuals in need thereof which is comprised of administering orally an effective amount of (−)-hydroxycitric acid.

4. The method of claim 1 where the (−)-hydroxycitric acid is supplied as a therapeutically effective amount of the free acid or its lactone.

5. The method of claim 1 where the (−)-hydroxycitric acid is supplied as a therapeutically effective amount of the alkali metal salts potassium or sodium (−)-hydroxycitrate.

6. The method of claim 1 where the (−)-hydroxycitric acid is supplied as a therapeutically effective amount of the alkaline earth metal salts calcium or magnesium (−)-hydroxycitrate.

7. The method of claim 1 where (−)-hydroxycitric acid is supplied as a therapeutically effective amount of a mixture the alkali metal salts and/or the alkaline earth metals of (−)-hydroxycitrate or some mixture of alkali metal salts and alkaline earth metal salts of (−)-hydroxycitrate or in the form of therapeutically effective amide and/or ester derivatives of (−)-hydroxycitric acid.

8. The method of claim 1 where the (−)-hydroxycitric acid is supplied as a therapeutically effective amount as the free acid, its lactone or as one or more of the salts or other derivatives of the free acid and is delivered in a controlled release form.

9. The method of claim 2 where the (−)-hydroxycitric acid is supplied as a therapeutically effective amount of the free acid or its lactone.

10. The method of claim 2 where the (−)-hydroxycitric acid is supplied as a therapeutically effective amount of the alkali metal salts potassium or sodium (−)-hydroxycitrate.

11. The method of claim 2 where the (−)-hydroxycitric acid is supplied as a therapeutically effective amount of the alkaline earth metal salts calcium or magnesium (−)-hydroxycitrate.

12. The method of claim 2 where (−)-hydroxycitric acid is supplied as a therapeutically effective amount of a mixture the alkali metal salts and/or the alkaline earth metals of (−)-hydroxycitrate or some mixture of alkali metal salts and alkaline earth metal salts of (−)-hydroxycitrate or in the form of therapeutically effective amide and/or ester derivatives of (−)-hydroxycitric acid.

13. The method of claim 2 where the (−)-hydroxycitric acid is supplied as a therapeutically effective amount as the free acid, its lactone or as one or more of the salts or other derivatives of the free acid and is delivered in a controlled release form.

14. The method of claim 3 where the (−)-hydroxycitric acid is supplied as a therapeutically effective amount of the free acid or its lactone.

15. The method of claim 3 where the (−)-hydroxycitric acid is supplied as a therapeutically effective amount of the alkali metal salts potassium or sodium (−)-hydroxycitrate.

16. The method of claim 3 where the (−)-hydroxycitric acid is supplied as a therapeutically effective amount of the alkaline earth metal salts calcium or magnesium (−)-hydroxycitrate.

17. The method of claim 3 where (−)-hydroxycitric acid is supplied as a therapeutically effective amount of a mixture the alkali metal salts and/or the alkaline earth metals of (−)-hydroxycitrate or some mixture of alkali metal salts and alkaline earth metal salts of (−)-hydroxycitrate or in the form of therapeutically effective amide and/or ester derivatives of (−)-hydroxycitric acid.

18. The method of claim 3 where the (−)-hydroxycitric acid is supplied as a therapeutically effective amount as the free acid, its lactone or as one or more of the salts or other derivatives of the free acid and is delivered in a controlled release form.

* * * * *